United States Patent [19]

Jalonen et al.

[11] Patent Number: 5,464,628
[45] Date of Patent: Nov. 7, 1995

[54] PHARMACEUTICAL COMPOSITIONS CONTAINING 4-SUBSTITUTED IMIDAZOLES TO BE ADMINISTERED TRANSDERMALLY

[75] Inventors: Harry Jalonen; Risto Lammintausta, both of Turku, Finland

[73] Assignee: Orion-yhtyma Oy, Espoo, Finland

[21] Appl. No.: 146,203

[22] PCT Filed: May 27, 1992

[86] PCT No.: PCT/FI92/00166

§ 371 Date: Nov. 12, 1993

§ 102(e) Date: Nov. 12, 1993

[87] PCT Pub. No.: WO92/21334

PCT Pub. Date: Dec. 10, 1992

[30] Foreign Application Priority Data

May 31, 1991 [GB] United Kingdom .................. 9111773

[51] Int. Cl.$^6$ ........................................................ A61F 13/02
[52] U.S. Cl. ......................... 424/448; 514/396; 514/944; 514/937; 514/969
[58] Field of Search ............................ 424/448; 514/396, 514/944, 937, 969

[56] References Cited

U.S. PATENT DOCUMENTS 5,124,157  6/1992  Colley ...................................... 424/448

FOREIGN PATENT DOCUMENTS 0413487  2/1991  European Pat. Off. .
0437030  7/1991  European Pat. Off. .

Primary Examiner—D. Gabrielle Phelan
Attorney, Agent, or Firm—Burns, Doane, Swecker & Mathis

[57] ABSTRACT

This invention relates to a transdermal preparation comprising a therapeutically active compound of the formula:

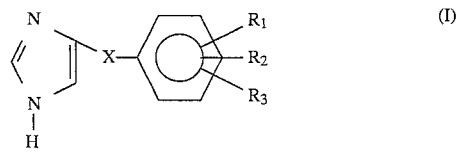

(I)

or

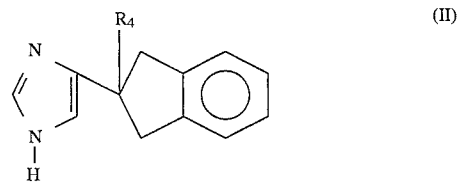 (II)

where $R_1$, $R_2$, and $R_3$, which can be the same or different are H, $CH_3$, $C_2H_5$ or Cl; X is CH=CH or $(CH_2)_n$ where n is 1 to 3 or X is —$C(OR_5)H$— where $R_5$ is methyl or ethyl; and $R_4$ is hydrogen or a straight alkyl of 1 to 4 carbon atoms. The transdermal administration of the compounds can be accomplished by preparations in the form of ointments, emulsions, lotions, solutions, creams or transdermal patches.

8 Claims, 1 Drawing Sheet

PHARMACEUTICAL COMPOSITIONS CONTAINING 4-SUBSTITUTED IMIDAZOLES TO BE ADMINISTERED TRANSDERMALLY

This invention relates to the use of certain known therapeutically active imidazoles substituted in the 4-position for use in the manufacture of pharmaceutical preparations for transdermal administration. Such transdermal preparations are also within the scope of the invention.

The therapeutically active 4-substituted imidazoles have the general formula

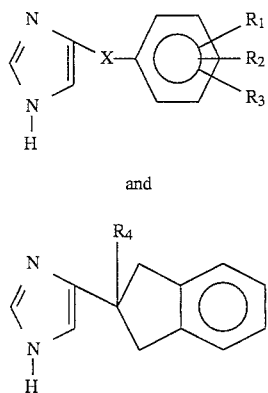

where $R_1$, $R_2$ and $R_3$ which can be the same or different are H, $CH_3$, $C_2H_5$ or Cl; X is CH=CH or $(CH_2)_n$ where n is 1 to 3 or X is —C($OR_5$)H— where $R_5$ is methyl or ethyl; and $R_4$ is hydrogen or a straight alkyl of 1 to 4 carbon atoms.

Members of formula (I) and (II) are well known potent and selective $α_2$-adrenoceptor active agents. Compounds of formula (I) are $α_2$-adrenoceptor agonists while compounds of formula (II) are $α_2$-adrenoceptor antagonists. Based on these pharmacological features the compounds are useful in a wide field of therapy. Compounds of formula (I) are disclosed e.g. in the European Patent Publications 24829, 34473, 34474, and 72615 and compounds of formula (II) are described in EP 198492. EP 24829 discloses various members of formula (I) having X being $CH_2$ or —C($OR_5$)H— as active antihypertensive, antiulcer, diuretic, tranquilizing, sedative, analgesic and anti-inflammatory agents. One member, 4-(2,3-dimethylbenzyl)-1H-imidazole, the generic name of which is detomidine, is commercially used as a veterinary sedative injection preparation to be used in the treatment of big animals, especially horses. EP 34473 discloses compounds of formula (I) where X is $(CH_2)_n$ and n is greater than 1 as valuable agents for the treatment of hypertension. EP 34474 discloses compounds of formula (I) where X is CH=CH as valuble antihypertensive, antithrombotic, antifungal and antimicrobial agents. EP 72615 describes i.a. compounds of formula (I) where X is —C($CH_3$)H— as useful antihypertensive agents. One member, 4-[α-methyl-2,3-dimethylbenzyl-1H-imidazole the generic name of which is medetomidine, has further been disclosed in U.S. Pat. No. 4,783,477 and has been commercialized as a veterinary sedative-analgesic injection preparation for small animals. EP 183492 discloses members of formula (II) as useful $α_2$-adrenoceptor antagonists. Atipamezole, which is the compound of formula (II) where $R_4$ is ethyl, is described in said patent to be useful for the reversal of detomidine. The compound is also marketed as an injection preparation for this purpose, especially as a reversal for medetomidine. EP 183492 suggests moreover a great many uses of the compounds of formula (II) e.g. antidiabetic, antidepressive and antiasthmatic uses.

In many therapeutic uses a steady, uniform administration of the active agent is desirable. Many compounds, especially those of formula (II) are known to have a rather poor bioavailability due to extensive initial metabolism of the drug. These compounds would not therefore be suitable for oral administration. In many fields of therapy injections are, however, not convenient. Transdermal administration is one alternative in such cases as it combines the convenience of oral administration and the high bioavailability of injections.

The present invention relates to transdermal administration of compounds of formula (I) and (II) as well as suitable preparation therefore.

Only a minor part of commercially available therapeutically active substances is suitable for transdermal administration due to many different pharmacokinetic and pharmacological reasons. One of the most limiting factors is, however, the physicochemical properties of the therapeutically active substance itself. For a compound to be able to penetrate the skin it must have both lipophilic (fat soluble) and hydrophilic (water soluble) properties in a suitable proportion. Such a suitable ratio between the lipophilic and hydrophilic properties is not very common for drug substances. The ability of a drug to penetrate through the skin can be predicted by its partition coefficient P in octanol/water. It is known that compounds having an optimal partition coefficient penetrate the skin better than compounds with either higher or lower partition coefficients. This optimal partition coefficient value is different for different kinds of compounds.

Compounds of formula (I) and (II) have proved to possess optimal partition coefficients thus rendering them suitable for transdermal administration.

BRIEF DESCRIPTION OF THE DRAWING

The transdermal administration of the compounds of formula (I) and (II) can be accomplished in two different ways: (i) by mixing the therapeutically active compounds with suitable pharmaceutical carriers and optionally penetration enhancers to form ointments, emulsions, lotions, solutions, creams, gels, patches or the like, where preferably a fixed amount of said preparation should be applied onto a certain area of skin, or (ii) by incorporating the therapeutically active substance into a transdermal delivery system according to one of the alternatives disclosed in FIGS. 1A, 1B and 1C. Transdermal drug delivery devices can be categorized into three general types (FIGS. 1A, 1B, and 1C).

Figure 1A:
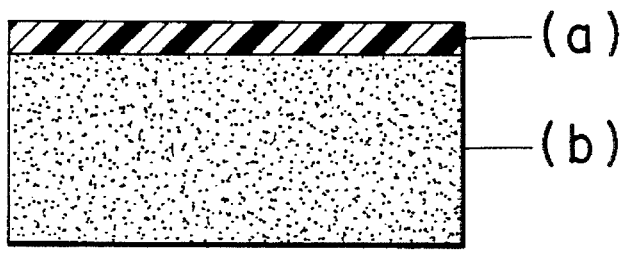
FIG. 1A discloses a transdermal device comprising (a) a drug impermeable backing layer and (b) an adhesive layer that fixes the bandage to the skin. In this preparation the drug is mixed in the adhesive layer.
Figure 1B:
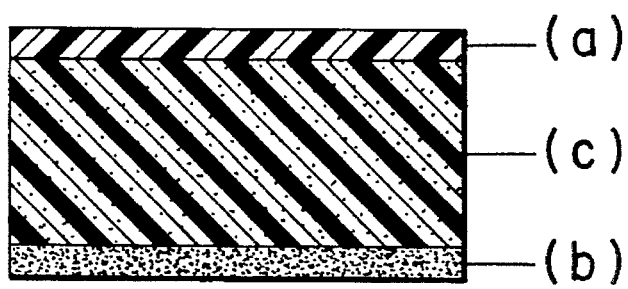
FIG. 1B represents a device incorporating a backing layer (a), an adhesive layer (b) and a matrix layer (c) preferably made of a polymer material in which the drug is dispersed. The rate of which the drug is released from the device is here controlled by the polymer matrix. A third kind of device is the reservoir system according to FIG. 1C comprising (a) a drug impermeable backing layer; an adhesive layer (b); a drug permeable membrane (d) sealed to one side of said backing layer as to define at least one drug reservoir compartment there between, and (e) a drug or composition thereof within said drug reservoir. In this case the drug in the reservoir is usually in liquid or gel form. The drug permeable membrane controls the rate at which the drug is delivered to the skin.
Figure 1C:
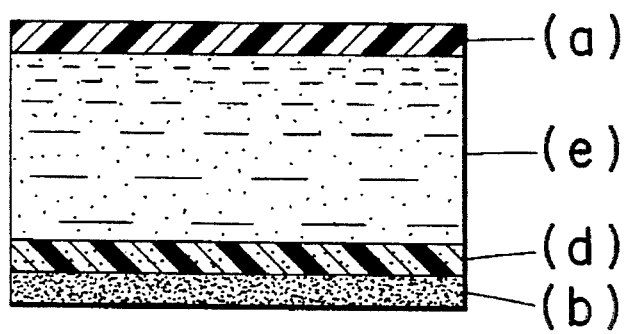

By the term "suitable pharmaceutical carrier" is meant a non-toxic pharmaceutically acceptable vehicle including for example polyethylene glycol, propylene glycol, isopropanol, ethanol, oleic acid, N-methylpyrrolidone, sesame oil, olive oil, wood alcohol ointments, vaseline and paraffin or a mixture thereof.

Suitable penetration enhancers include for example saturated and unsaturated fatty acids and their esters, alcohols, monoglycerides, diethanolamines, N,N-dimethylamines such as linolenic acid, linolenyl alcohol, oleic acid, oleyl alcohol, stearic acid, stearyl alcohol, palmitic acid, palmityl alcohol, myristic acid, myristyl alcohol, 1-dodecanol, 2-dodecanol, lauric acid, decanol, capric acid, octanol, caprylic acid, 1-dodecylazacycloheptan-2-one sold under the trademark AZONE, ethyl caprylate, isopropyl myristate, hexamethylene lauramide, hexamethylene palmitate, capryl alcohol, decyl methyl sulfoxide, dimethyl sulfoxide, salicylic acid and its derivatives, N,N-diethyl-m-toluamide, crotamiton, 1-substituted azacycloalkan-2-ones, polyethylene glycol monolaurate and any other compounds compatible with the therapeutically active compounds of formula (I) and (II) and the packages and having transdermal permeation enhancing activity.

Preferred administration rates of the drug is 0.1–1000 µg/h through a skin area of about 2–90 cm$^2$, preferably 10–30 cm$^2$. The amount of drug delivered into the skin can be controlled by a number of factors including skin patch size, degree of drug loading, the use of rate controlling membranes, permeation enhancers etc.

The backing layer can be flexible or nonflexible and suitable materials include for example cellophane, cellulose acetate, ethylcellulose, vinylacetate-vinylchloride copolymers, polyethylene terephthalate, nylon, polyethylene, polypropylene, polyester films, polyvinylidene chloride, coated flexible fibrous backings such as paper and cloth and aluminium foil.

The adhesive layer comprises for example polysiloxanes, polyisobutylenes, polyacrylates, polyurethanes, ethylene-vinyl acetate copolymers, polyether amide block polymers, polyisobutene, polystyrene-isoprene copolymers, polystyrene-butadiene copolymers. Preferred adhesives are acrylates, silicones and polyurethanes.

The drug permeable membrane can be made of materials including polyethylene, polypropylene, ethylene vinyl acetate copolymers, polycarbonates, polyvinyl chloride, polyacrylate polymers, polysulfone polymers, polyvinylidienes, polyvinylidenes, polyesters and polyisobutylenes, for example.

The matrix is preferably an anhydrous matrix such as natural or synthetic rubbers or other polymeric material, thickened mineral oil or petroleum jelly, for example. A preferred embodiment is an ethylene/vinylacetate copolymer.

EXPERIMENTS

Analytical HPLC Method

The fully automated (Hewlett-Packard, USA) liquid chromatograph consisted of a pump 1090, an autosampler and autoinjector (79847A) and a fixed wavelength UV detector, 210 nm (79881A). The chromatograms, retention times and peak areas were recorded with an integrator 3393. The separations were carried out at a column temperature of 37° C. on a 35 * 4.6 mm stainless steel column (packed with a 3-µm spherical octadecyl-silane-bonded silica particles; HS-3 C-18, (Perkin-Elmer, USA). The mobile phase consisted of different mixtures of acetonitrile: 0.05M aqueous phosphate buffer pH 7.4 containing 0.004M of dimethyloctyl amine. The flow rate was 0.8 ml/min.

Shake-flask Apparent Partition Coefficient Method

The apparent partition coefficient P' (the partition coefficient P for ionic compounds in partly ionized state) was determined for the different arylalkyl imidazole compounds at different pH- values (7.4, 3.0, about 5, 7 and 9) according to the following procedure: the compounds were dissolved in octanol-saturated phosphate buffer (0.1M, with the appropriate pH) using as a modified method the one described for clonidine and structurally related imidazoles (Timmermans et al Naunyn-Schmid. Arch. Pharmacol. 300, p. 217, 1977) the starting concentrations in the aqueous phosphate buffer being 200 µM. The aqueous phase was shaken with buffer-saturated n-octanol (the volumes being for aqueous buffer and octanol either 10:1 or 20:1) for one hour at room temperature (20°–22° C.) and then equilibrated by allowing to stand for 20 hours. At least three parallel tests were made in each case. Samples were taken from the aqueous phase and the concentration of the compound was analyzed according to the HPLC method described above. The apparent partition coefficient (P') at a certain pH can be calculated from the following equation:

$$P'=(C_0-C_1)V_{Aq}/C_1 V_{Oct}$$

$C_0$ is the initial and $C_1$ is the final (after partioning) concentration of the tested compound in the aqueous phase. $V_{Aq}$ and $V_{Oct}$ are the volumes of the aqueous respectively the octanol phase.

IN VITRO SKIN PERMEATION MEASUREMENTS

Treatment of Skin Samples

All of the penetration and skin/solvent partition experiments reported here utilized human skin from the thigh region obtained at autopsy. The skin samples (with the thickness of about 1 mm) containing the epidermis and a part of dermis were taken with a dermatome (Elemo HM94, Switzerland). The epidermis was separated from the dermis by the method of Chandrasekaran et al (Am. I. Chem. Eng. J. 22 p. 828, 1976) by keeping the skin in hot water (60° C.) for 60 seconds. After isolation the epidermis was dried between two sheets of paper, cut into smaller pieces and stored in aluminium foil in polyethylene bags at 4° C. for no more than 4 weeks.

Permeation Experiments

Two different kinds of diffusion cells were used in the experiments: Franz type of diffusion cell, finite dose technique (Franz, Curr. Probl. Dermatol. 7, p. 58, 1978), (FDC-400, diffusion area 1.77 cm$^2$, receiver compartment volume 11.5–12.0 ml, Crown Glass Company, Inc. USA) was used for the testing of the ointment and for the polymer formulation. For all the other experiments diffusion cells of type DC 100B Side-Bi-Side was used, diffusion area 0.79 cm$^2$, donor and receiver compartment volume 3.4 ml, Crown Glass Company Inc. USA. The stirring (500 rpm) of the magnet bar was generated for both type of cells with a drive console (VSG-1, Crown Glass Company Inc. USA). Both types of cells were made of glass and were jacketed for temperature control 37° C. (MGW Lauda, type MS, Germany).

The stored skin (epidermis) samples were checked visually and microscopically for defects before use. In the permeation experiment the epidermis sample was clamped between the two parts of the cell system. To be able to prevent any leakages the four corners of the epidermis sample extended outside the contact area of the system. The epidermis sample was hydrated from both sides over night, with aqueous phosphate buffer 0.05M pH 7.4 (6.9 g $NaH_2PO_4*H_2O/l$ of water, pH adjusted to 7.4 with 10M NaOH) on the receiver side (viable epidermis side) and on the donor side (stratum corneum side) with the same solvent, ointment or patch (without the penetrant) to be used as the donor formulation of the penetrant in the actual skin permeation experiment. Next morning after hydrating the skin overnight the permeation experiment started by first removing the donor formulation and the receiver solutions from the diffusion cell: fresh aqueous phosphate buffer pH 7.4 was added to the receiver side (FDC-400 11.5 ml and DC 100B 3.4 ml) and a formulation volume now containing a known amount of penetrant molecule was added to the donor side. Particular care was taken to prevent air bubbles from forming on the surface of the skin. 1.0 ml samples (DC 100B) and 0.4 ml (FDC-400) were withdrawn from the receiver chamber at intervals and replaced with the same volume of fresh receiver solution. The samples were then analyzed according to the HPLC method described above. Corrections were made (for the losses from earlier samplings) in calculating the cumulative amount of drug that permeated the skin. The permeation of the penetrant through epidermis was described by a plot of cumulated amount of penetrant Q (in µg) vs time in hours. The slope of the curve and the intercept on the x-axis (lag time) were determined by linear regression. Penetrant flux J (in $µg/cm^2h$) was calculated from the slope µg penetrant/h and knowing the area of the skin surface through which diffusion was taking place ($cm^2$) (Flynn et al, CRC Press, Boca Raton, Fla., p. 45, 1987). The permeability constant $k_p$ was calculated from the formula $k_p=J/C$ where J represents the steady-state flux and C the donor concentrations. The results are presented in Tables I to VII.

Three different kinds of ointments of two of the compounds tested (code nr 253 AII and 1248) were prepared: an aqueous ointment (1), a hydrophilic (2) and a lipophilic (3) one, VI—VI. Table VII discloses an example of a patch formulation illustrating the invention.

TABLE I

Molecular structure of arylalkyl imidazole compounds tested.

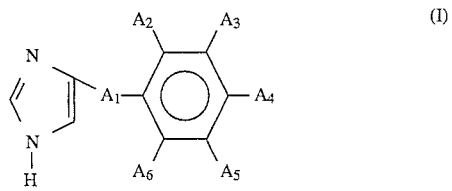

(I)

| No | Compound | $A_1$ | $A_2$ | $A_3$ | $A_4$ | $A_5$ | $A_6$ |
|----|----------|-------|-------|-------|-------|-------|-------|
| 1  | 247 AII  | $CH_2$ | H | H | H | $CH_3$ | H |
| 2  | 248 AII  | $CH_2$ | H | H | $CH_3$ | H | H |
| 3  | 207 AIV  | $CH_2$ | $CH_3$ | H | H | H | $CH_3$ |
| 4  | 253 AII  | $CH_2$ | H | H | H | $CH_3$ | $CH_3$ |
| 5  | 867 AII  | $CH_2$ | H | $CH_3$ | H | H | $CH_3$ |
| 6  | 254 AII  | $CH_2$ | H | H | $CH_3$ | $CH_3$ | H |
| 7  | 257 CIII | $CH_2$ | Cl | H | H | H | Cl |
| 8  | 207 AVI  | $OC_2H_5$ $|$ CH | $CH_3$ | H | H | H | $CH_3$ |
| 9  | 1248 atipamezole | | | | | | |
| 10 | 305 BII  | CH=CH | $CH_3$ | H | H | H | $CH_3$ |
| 11 | 304 AII  | $(CH_2)_3$ | $CH_3$ | H | H | H | $CH_3$ |

TABLE I-continued

Molecular structure of arylalkyl imidazole compounds tested.

| No | Compound | $A_1$ | $A_2$ | $A_3$ | $A_4$ | $A_5$ | $A_6$ |
|----|----------|-------|-------|-------|-------|-------|-------|
| 12 | 1424 AII | $CH_2$ | H | H | H | Cl | Cl |

TABLE II

Effect of pH of the donor solution on the percutaneous absorption of 253 AII through human cadaver epidermis at 37° C.

| pH | Conc. mg/ml | Ioniz. degree % | Flux ± SD $µg/cm^2$ h | $k_p*10^{-4}$ cm/h | Enhanc. factor | Log P' |
|----|-------------|-----------------|-----------------------|--------------------|----------------|--------|
| 3.0 | 245.00 | 100.0 | 1.07 ± 0.33 | 0.04 | 1 | -0.66 |
| 5.1 | 34.39  | 98.9  | 2.13 ± 0.48 | 0.62 | 14 | 0.67 |
| 6.9 | 1.00   | 59.1  | 1.73 ± 0.15 | 17.25 | 394 | nd |
| 8.8 | 0.45   | 1.8   | 1.73 ± 0.47 | 38.65 | 883 | 2.81 |

TABLE III

Effect of pH of the donor solution on the percutaneous penetration of 1248 through human cadaver skin at 37° C.

| pH | Conc. mg/ml | Ioniz. degree % | Flux ± SD $µg/cm^2$ h | $k_p*10^{-4}$ cm/h | Enhanc. factor | Log P' |
|----|-------------|-----------------|-----------------------|--------------------|----------------|--------|
| 3.0 | 35.20 | 100.0 | 0.09* | <0.03 | 1 | -0.33 |
| 5.0 | 10.18 | 99.2  | 0.37 ± 0.03 | 0.37 | 14 | 1.02 |
| 7.4 | 0.30  | 33.4  | 1.55 ± 0.31 | 52.30 | 1958 | 3.05 |
| 9.1 | 0.10  | 1.0   | 0.52 ± 0.14 | 53.47 | 2002 | 3.66 |

*n = 1
The enhancing factor in Tables II to III is calculated as the ratio $k_p*10^{-4}$ at pH 3.0:$k_p*10^{-4}$ at the current pH

TABLE IV

Percutaneous penetration parameters and skin: buffer partition coefficients log P' of arylalkyl imidazole compounds through human cadaver epidermis at pH 7.4, 37° C.

| No | Compound | Flux ± SD $µg/cm^2$ h | Lag time h | $k_p*10^{-3}$ cm/h | Log P' |
|----|----------|-----------------------|------------|--------------------|--------|
| 1  | 247 AII  | 26.7 ± 5.4 | 1.0 | 5.5  | 2.21 |
| 2  | 248 AII  | 27.1 ± 2.2 | 1.0 | 5.9  | 2.26 |
| 3  | 207 AIV  | 40.3 ± 0.4 | 1.0 | 10.1 | 2.55 |
| 4  | 253 AII  | 4.0 ± 0.6  | 3.0 | 2.7  | 2.50 |
| 5  | 867 AII  | 13.0 ± 4.2 | 2.0 | 6.8  | 2.54 |
| 6  | 254 AII  | 36.8 ± 2.9 | 1.3 | 14.7 | 2.54 |
| 7  | 257 CIII | 2.9 ± 0.7  | 1.7 | 2.8  | 2.96 |
| 8  | 207 AVI  | 1.9 ± 0.2  | 2.0 | 1.6  | 2.65 |
| 9  | 1248     | 1.6 ± 0.3  | 2.9 | 4.1  | 3.05 |
| 10 | 305 BII  | 4.9 ± 0.6  | 1.0 | 11.9 | 3.00 |
| 11 | 304 AIII | 13.8 ± 3.3 | 1.0 | 27.5 | 3.08 |
| 12 | 1424 AII | 3.7 ± 0.2  | 1.8 | 12.5 | 3.55 |

TABLE V

Permeation of 253 AII through human cadaver skin at 37° C. from different ointment formulations.

| Formulation | | Flux µg/cm² h | kp*10⁻⁶ cm/h |
|---|---|---|---|
| 1. | | | |
| 253 AII base | 50 mg | 0.458 | 9.2 |
| Ol. arach.(a) | 100 mg | | |
| Cetylan(b) | 100 mg | | |
| Aq. dest.(c) | 750 mg | | |
| 2. | | | |
| 253 AII | 50 mg | 0.066 | 1.3 |
| PEG 1500(d) | 60 mg | | |
| PEG 400(e) | 120 mg | | |
| 3. | | | |
| 253 AII base | 50 mg | 1.965 | 39.3 |
| Vaselin alb. | 710 mg | | |
| Paraffin liq. | 240 mg | | |

(a) Oleum arachideum
(b) Cetylan, an emulgating wax
(c) Distilled water
(d) Polyethylene glycol of average mol. weight 1500
(e) Polyethylene glycol of average mol. weight 400

TABLE VI

Permeation of 1248 through human cadaver skin at 37° C. from different ointment formulations.

| Formulation | | Flux µg/cm² h | kp*10⁻⁶ cm/h |
|---|---|---|---|
| 1. | | | |
| 1248 base | 50 mg | 0.855 | 17.1 |
| Ol. arach. | 100 mg | | |
| Cetylan | 100 mg | | |
| Aq. dest. | 750 mg | | |
| 2. | | | |
| 1248 base | 50 mg | 0.053 | 1.1 |
| PEG 1500 | 60 mg | | |
| PEG 400 | 120 mg | | |
| 3. | | | |
| 1248 base | 50 mg | 2.217 | 42.6 |
| Vaselin alb. | 710 mg | | |
| Paraffin liq. | 240 mg | | |

TABLE VII

Example representing a transdermal patch

| Composition | |
|---|---|
| A compound described in Table I either as a free base or as a pharmaceutically acceptable salt thereof | 1–20% |
| Vaselin alb. | about 20% |
| Paraffin | about 5% |
| Silastic Elastomer 382 Medical grade* | about 55% |

*Dow Corning Corporation, USA

The compound is added under thorough mixing to a mixture of vaselin and paraffin (mixture I). The silastic elastomer is weighed directly to a tared mould to which mixture I is added and mixed throughly before adding the curing agent, catalyst M (Dow Corning). The formulation is allowed to cure for 48 h at room temperature and protected from light.

This formulation gives a flux rate through the skin in the range of 0.1 to 2 µg/cm²h for the compounds as defined in claim 1.

We claim:

1. A transdermal preparation comprising a therapeutically active compound of the formula

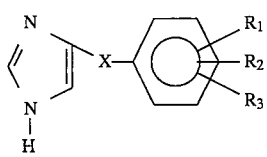

or

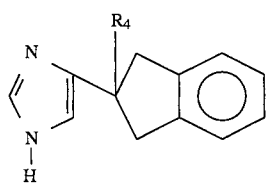

where $R_1$, $R_2$ and $R_3$ which can be the same or different are H, $CH_3$, $C_2H_5$ or Cl; X is CH=CH or $(CH_2)_n$ where n is 1 to 3; and $R_4$ is hydrogen or a straight alkyl of 1 to 4 carbon atoms.

2. A preparation according to claim 1 which is in the form of an ointment, emulsion, gel, lotion, solution or cream.

3. A preparation according to claim 1 where the preparation is a transdermal delivery system comprising a drug impermeable backing layer and an adhesive layer where the drug is dispersed in the adhesive layer.

4. A preparation according to claim 1 where the preparation is a transdermal delivery system comprising a drug impermeable backing layer; an adhesive layer and a matrix layer in which the drug is dispersed.

5. A preparation according to claim 4 where the matrix layer is made of a polymer material.

6. A preparation according to claim 1 where the preparation is a transdermal delivery system comprising a drug impermeable backing layer; an adhesive layer; a drug permeable membrane sealed to one side of said backing layer as to define at least one drug reservoir compartment therebetween and a drug or composition thereof within said drug reservoir.

7. A preparation according to claim 1 wherein $R_1$ is Cl and $R_2$ and $R_3$ which can be the same or different are H, $CH_3$, $C_2H_5$ or Cl.

8. A preparation according to claim 1 wherein the therapeutically active compound is from Group (II).

* * * * *